US00PP13701P29

(12) United States Plant Patent
Heims

(10) Patent No.: US PP13,701 P2
(45) Date of Patent: Apr. 1, 2003

(54) X HEUCHERELLA PLANT NAMED 'CHOCOLATE LACE'

(75) Inventor: Daniel M. Heims, Portland, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 10/079,438

(22) Filed: Feb. 19, 2002

(51) Int. Cl.[7] ..... A01H 5/00
(52) U.S. Cl. ..... Plt./263
(58) Field of Search ..... Plt./263

*Primary Examiner*—Bruce R. Campell
*Assistant Examiner*—Annette H. Para
(74) *Attorney, Agent, or Firm*—Klarquist Sparkman LLP

(57) ABSTRACT

A new and distinct hybrid of x Heucherella plant characterized by its distinctive lacy, dark foliage, compact habit, and striking white flowers on dark peduncles.

1 Drawing Sheet

Botanical classification: x Heucherella.
Variety denomination: 'Chocolat Lace'.

BACKGROUND OF THE INVENTION

The present invention relates to a new and distinct intergeneric hybrid between Heuchera and Tiarella, known by the cultivar name 'Chocolate Lace'. Both genera, Heuchera and Tiarella, are of the family Saxifragaceae. This intergeneric hybrid is known as x Heucherella.

This new cultivar originated from a mass pollination using Heuchera as the seed parent and Tiarella as the pollen parent. Pollen from selected proprietary Tiarella from interspecfic crosses was massed onto plants of selected proprietary Heuchera from interspecific crosses and all the seed massed together. As such, no species designations are given.

SUMMARY OF THE INVENTION

This new Heucherella is distinguished by:

1. Small, milk chocolate colored leaves shaped like a lacy hawthorn leaf.

2. Striking, red brown peduncles and pedicels.

3. Small, nodding starry white flowers.

4. Repeat blooming, which extends the bloom time.

5. Tight habit.

The new variety has been reproduced only by asexual propagation (division and tissue culture). Each of the progeny exhibits identical characteristics to the original plant. Asexual propagation by division and tissue culture using standard micropropagation techniques with terminal and lateral shoots as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWING

The drawing shows the new plant growing in a one-gallon pot in Canby, Oreg.

DETAILED PLANT DESCRIPTION

The following is a detailed description of the new x Heucherella hybrid based on observations of three-year-old specimens grown in the field in Canby, Oreg. The color descriptions are all based on The Royal Horticultural Society Colour Chart.

Botanical: x Heucherella.
Cultivar name: 'Chocolate Lace'.
Plant:
- *Type.*—Herbaceous perennial.
- *Form.*—Basal rosette.
- *Hardiness.*—USDA Zone 5.
- *Size.*—20 cm tall and 35 cm wide.

Leaf:
- *Type.*—Simple.
- *Arrangement.*—Rosette.
- *Shape.*—Ovate.
- *Lobing/division.*—5 to 7 scalloped lobes, the terminal lobe cut almost to the base and the secondary lobes cut half way to the base. Main lobes are close together. Lobes themselves are lobed and crenate.
- *Venation.*—Palmate.
- *Margins.*—Crenate.
- *Apex.*—Mucronulate.
- *Base.*—Cordate.
- *Blade size.*—6.6 cm long and 6 cm wide.
- *Aspect.*—Glossy new leaves and matte old leaves.
- *Texture.*—Puberulous and with glandular hairs. Margins and vein undersides hispid.
- *Petiole length.*—10 to 12.3 cm.
- *Petiole texture.*—Hispid and with glandular hairs.
- *Petiole color.*—On young leaf Greyed Orange 177A to Grey Brown 199B on older leaf.
- *Leaf color.*—New spring leaves — Between Greyed Purple 187A and Brown 200B. Spring leaves — Abaxial side — Brown 200B. Adaxial side — Closest to Greyed Purple 187A. Winter leaves — Grey Brown — Closest to Grey 200A.

Inflorescence:
- *Type.*—Thyrse.
- *Number of flowers.*—About 100 per thyrse.
- *Peduncle.*—With 1 to 2 leaves and branches. Height — 33 cm. Diameter — 0.15 cm. Color — Brown 200D. Vestiture — Glandular hairs.

*Pedicel*.—Length — to 0.35 cm. Vestiture — Glandular hairs. Color — Greyed Purple187A.

*Bloom period*.—May to frost in Canby, Oreg.

Flower bud:

*Size*.—0.5 cm deep and 0.2 cm wide.

*Description*.—Glandular hairs, downfacing.

*Color*.—Overall a grey pink. Greyed Orange 177C at tips and Red 49C at base.

Flower:

*Type*.—Perfect, zygomorphic, sepals petaloid.

*Shape*.—Rotate.

*Size*.—1 cm wide and 0.4 cm deep.

*Petal count*.—5.

*Petal shape*.—Obovate with a clawed base.

*Petal size*.—0.6 cm long and 1.5 cm wide.

*Petal color*.—White 55D.

*Petal texture*.—Satiny.

*Calyx*.—Petaloid, divided ⅔ way to the base, with glandular hairs.

*Calyx shape*.—Campanulate with 5 rounded lobes.

*Calyx size*.—0.5 cm wide and 0.4 cm deep.

*Calyx texture*.—Glandular pubescent.

*Calyx color*.—Outside: Very light pink at base. Red 56D. Tips are Pink (Red 54D) or Brown (Greyed Orange 177C). Inside: Very light pink (Red 49D) with Green (Yellow Green 148B) and sometimes a little Brown 200C tips.

*Stamen number*.—5, sterile.

*Pistil*.—Very light pink. Red 49D.

*Fragrance*.—None.

*Lastingness*.—A thyrse blooms for about 2 weeks on the plant.

Fruit and seed: None, plant does not form fruit or seed.

*Fertility*.—Sterile.

Disease tolerance: Excellent disease resistance.

COMPARISONS TO SIMILAR X HEUCHERELLA

Compared to x Heucherella 'Burnished Bronze', (U.S. Plant Pat. No. 12,159), this new cultivar is more compact with shorter, darker flowering stems and smaller leaves, more cut, lacier leaves. The new cultivar has browner flower buds and larger flowers.

Compared to x Heucherella 'Cinnamon Bear', an unpatented plant, this new cultivar has leaves that are smaller, more lobed and crenate and the main lobes are closer together. The new cultivar has darker flower buds, calyces, and peduncles and the leaf is smaller.

I claim:

1. A new and distinct hybrid of x Heucherella plant substantially as shown and described.

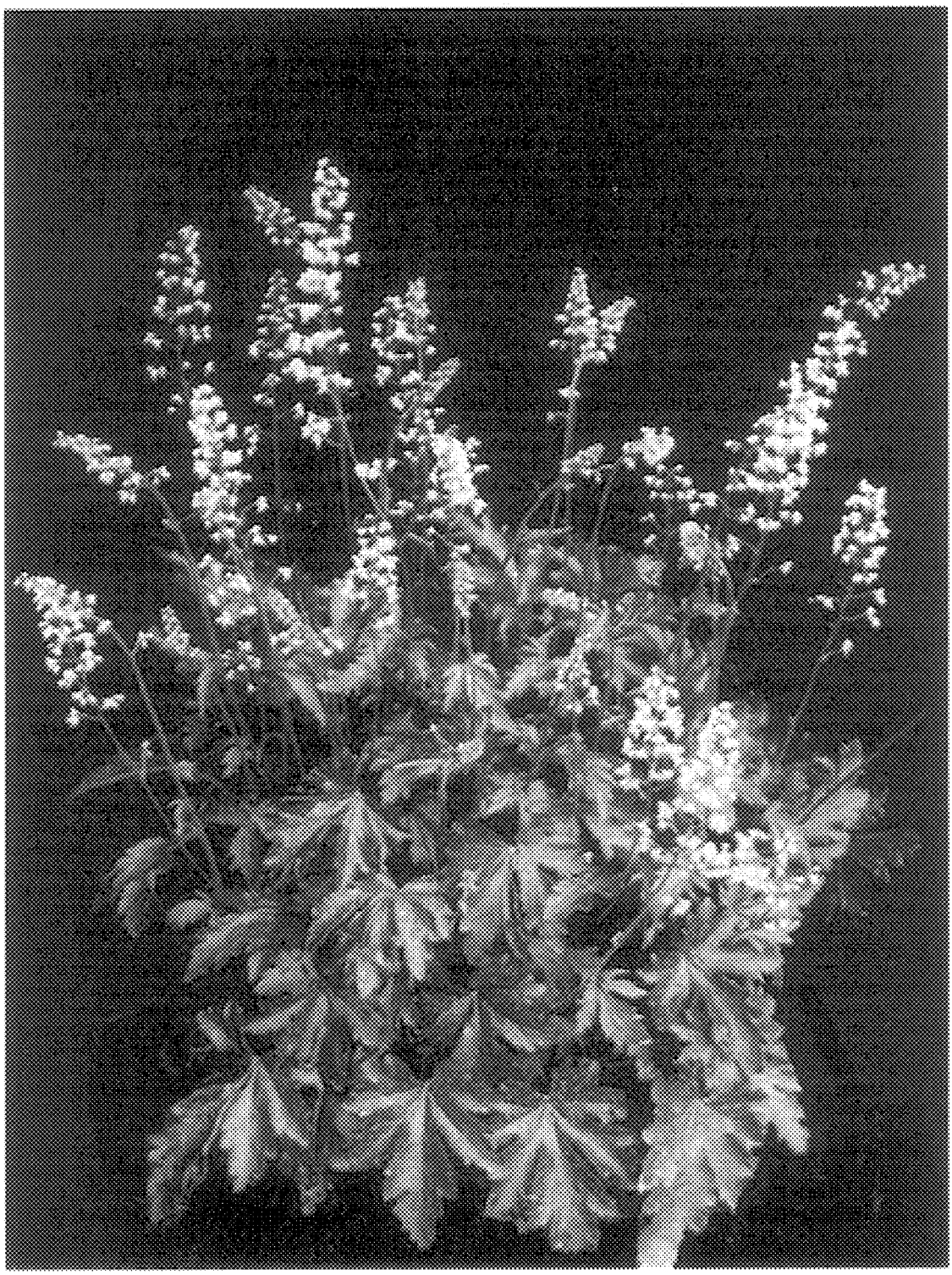

* * * * *